US012773117B2

(12) United States Patent
Qiu et al.

(10) Patent No.: US 12,773,117 B2
(45) Date of Patent: Oct. 27, 2026

(54) WEARABLE SYSTEM BLOOD PRESSURE MEASUREMENTS

(71) Applicant: BIOINTELLISENSE, INC., Golden, CO (US)

(72) Inventors: Zongde Qiu, Cupertino, CA (US); David Jonq Wang, Palo Alto, CA (US); James Mault, Evergreen, CO (US)

(73) Assignee: BIOINTELLISENSE, INC., Golden, CO (US)

( * ) Notice: Subject to any disclaimer, the term of this patent is extended or adjusted under 35 U.S.C. 154(b) by 56 days.

(21) Appl. No.: 18/299,565

(22) Filed: Apr. 12, 2023

(65) Prior Publication Data

US 2023/0320602 A1 Oct. 12, 2023

Related U.S. Application Data

(60) Provisional application No. 63/362,872, filed on Apr. 12, 2022.

(51) Int. Cl.
*A61B 5/022* (2006.01)
*A61B 5/00* (2006.01)
(Continued)

(52) U.S. Cl.
CPC .......... *A61B 5/022* (2013.01); *A61B 5/02125* (2013.01); *A61B 5/02416* (2013.01);
(Continued)

(58) Field of Classification Search
CPC . A61B 5/022; A61B 5/02125; A61B 5/02416; A61B 5/318; A61B 5/7221;
(Continued)

(56) References Cited

U.S. PATENT DOCUMENTS 10,485,463 B2 11/2019 Dietiker
10,709,339 B1 * 7/2020 Lusted .................. A61B 5/282
(Continued)

OTHER PUBLICATIONS

Chen MW, Kobayashi T, Ichikawa S, Takeuchi Y, Togawa T (2000), Continuous estimation of systolic blood pressure using the pulse arrival time and intermittent calibration, Med Biol Eng Comput 38(5):569-574.
(Continued)

*Primary Examiner* — Dixomara Vargas
(74) *Attorney, Agent, or Firm* — Maschoff Brennan

(57) ABSTRACT

In an example, a method to monitor blood pressure of a subject includes: generating a first signal representing cardiac electrical activity of the subject using a first sensor of a wearable system; generating a second signal representing cardiac photonic activity of the subject using a second sensor of the wearable system; generating a third signal representing cardiac mechanical activity of the subject using a third sensor of the wearable system; determining from the third signal a time period during which the first and second signals are likely clean; extracting one or more features from portions of two or more of the first, second, or third signals corresponding to the time period, the one or more extracted features including at least one of a PTT, a PAT, or BVE features; and determining a current blood pressure of the subject based on the one or more extracted features.

26 Claims, 8 Drawing Sheets

(51) Int. Cl.
*A61B 5/021* (2006.01)
*A61B 5/024* (2006.01)
*A61B 5/318* (2021.01)

(52) U.S. Cl.
CPC ............ *A61B 5/318* (2021.01); *A61B 5/7221* (2013.01); *A61B 2560/0223* (2013.01); *A61B 2562/0219* (2013.01); *A61B 2562/06* (2013.01)

(58) Field of Classification Search
CPC .... A61B 2560/0223; A61B 2562/0219; A61B 2562/06
See application file for complete search history.

(56) References Cited

U.S. PATENT DOCUMENTS

| | | | | |
|---|---|---|---|---|
| 10,743,091 | B1 | 8/2020 | Wang et al. | |
| 10,973,414 | B2 * | 4/2021 | Moon | A61B 5/6826 |
| 11,172,909 | B2 | 11/2021 | Chan et al. | |
| 11,317,805 | B2 * | 5/2022 | Gosink | A61B 5/681 |
| 2010/0160798 | A1 * | 6/2010 | Banet | A61B 5/02125 600/490 |
| 2017/0238819 | A1 * | 8/2017 | Waller | A61B 5/4875 |
| 2018/0104502 | A1 * | 4/2018 | Perschbacher | A61B 5/361 |
| 2018/0256059 | A1 * | 9/2018 | Perschbacher | A61B 5/7232 |
| 2018/0360323 | A1 * | 12/2018 | Lui | A61B 5/02438 |
| 2019/0167142 | A1 * | 6/2019 | Perschbacher | A61B 5/363 |
| 2019/0320916 | A1 * | 10/2019 | Banet | A61B 5/02133 |
| 2020/0077914 | A1 * | 3/2020 | Siejko | A61B 5/352 |
| 2020/0100693 | A1 * | 4/2020 | Velo | G16H 50/20 |
| 2020/0288990 | A1 * | 9/2020 | Remme | A61B 5/0031 |
| 2020/0312453 | A1 * | 10/2020 | Raisanen et al. | G06F 3/016 |
| 2020/0367760 | A1 * | 11/2020 | Klaassen | A61B 5/021 |
| 2021/0000347 | A1 * | 1/2021 | Stump | A61B 5/1102 |
| 2021/0000353 | A1 * | 1/2021 | Fujii | A61B 5/02125 |
| 2021/0169417 | A1 * | 6/2021 | Burton | A61B 5/4857 |
| 2021/0233656 | A1 * | 7/2021 | Tran | A61B 5/7275 |
| 2021/0251501 | A1 * | 8/2021 | Moon | A61B 5/746 |
| 2021/0386300 | A1 * | 12/2021 | Rogers | A61B 5/746 |
| 2022/0117553 | A1 * | 4/2022 | Chahine | A61B 5/0535 |
| 2022/0142493 | A1 * | 5/2022 | Albert | A61B 5/7278 |
| 2022/0167857 | A1 * | 6/2022 | Lin | G16H 40/63 |
| 2022/0175258 | A1 * | 6/2022 | Kitchens | A61B 5/02116 |
| 2022/0233191 | A1 * | 7/2022 | Shelton, IV | G16H 40/63 |
| 2022/0238235 | A1 * | 7/2022 | Shelton, IV | A61B 10/0012 |
| 2022/0240869 | A1 * | 8/2022 | Shelton, IV | A61B 5/4337 |
| 2022/0241028 | A1 * | 8/2022 | Shelton, IV | A61B 5/02055 |
| 2022/0241474 | A1 * | 8/2022 | Shelton, IV | G16H 50/20 |
| 2022/0241601 | A1 * | 8/2022 | Cowan | A61N 1/3987 |
| 2022/0401037 | A1 | 12/2022 | Sadeghzadeh et al. | |
| 2023/0263482 | A1 * | 8/2023 | Kostense | G16H 20/60 705/3 |
| 2023/0371821 | A1 * | 11/2023 | Zhang | A61B 5/7203 |
| 2024/0197186 | A1 * | 6/2024 | Agrawal | A61B 5/6826 |
| 2024/0210359 | A1 * | 6/2024 | Agrawal | G01N 29/2418 |
| 2024/0315575 | A1 * | 9/2024 | Parkka et al. | A61B 5/021 |
| 2024/0315578 | A1 * | 9/2024 | Rantanen | A61B 5/7282 |

OTHER PUBLICATIONS

Escobar B, Torres R (2014), Feasibility of non-invasive blood pressure estimation based on pulse arrival time: a MIMIC database study, In: Computing in cardiology 2014, Sep. 7-10, 2014, pp. 1113-1116.
Feng, Jingjie & Huang, Zhongyi & Congcong, Zhou & Ye, Xuesong (2018), Study of continuous blood pressure estimation based on pulse transit time, heart rate and photoplethysmography-derived hemodynamic covariates, Australasian Physical & Engineering Sciences in Medicine. 41. 10.1007/s13246-018-0637-8.
Gesche H, Grosskurth D, Kuchler G, Patzak A (2012), Continuous blood pressure measurement by using the pulse transit time: comparison to a cuff-based method. Eur J Appl Physiol 112(1):309-315.
Poon CCY, Zhang YT (2005), Cuff-less and noninvasive measurements of arterial blood pressure by pulse transit time, In: 2005 IEEE Engineering in Medicine and Biology 27th annual conference, Jan. 17-18, 2006, pp. 5877-5880).
Zheng YL, Yan BP, Zhang YT, Poon CCY (2014), An armband wearable device for overnight and cuff-less blood pressure measurement, IEEE Trans Biomed Eng 61(7):2179-2186.
What Can We Do With Pulse-Transit-Time Calculations from Wearables, Electric Design, retrieved from https://www.electronicdesign.com/industrial-automation/articles/21808496 . . . Jan. 27, 2022, 12 pgs.

* cited by examiner

WEARABLE SYSTEM BLOOD PRESSURE MEASUREMENTS

CROSS-REFERENCE TO RELATED APPLICATION

This application claims the benefit of and priority to U.S. Provisional App. No. 63/362,872 filed Apr. 12, 2022 which is incorporated herein by reference in its entirety.

FIELD

The embodiments discussed herein are related to wearable system blood pressure measurements.

BACKGROUND

Unless otherwise indicated herein, the materials described herein are not prior art to the claims in the present application and are not admitted to be prior art by inclusion in this section.

Blood pressure is one of the vital signs-together with respiratory rate, heart rate, oxygen saturation, and body temperature—that healthcare professionals often use in evaluating a subject's health. A normal resting blood pressure in an adult is approximately 120 millimeters (mm) of mercury (Hg) (or 16 kilopascals (kPa)) systolic over 80 mm of Hg (or 11 kPa) diastolic, denoted as "120/80 mmHg".

A sphygmomanometer is an example of a blood pressure monitor that may be used to measure a subject's blood pressure. A sphygmomanometer consists of an inflatable cuff, a measuring unit (e.g., a mercury manometer or aneroid gauge), and a pump (e.g., manually operated bulb and valve or an electrically operated pump). Blood pressure measurements using a sphygmomanometer are typically more accurate if the subject is stationary and calm. In addition, sphygmomanometers are typically not very portable. Due to their nature and method of use, sphygmomanometers are unsuitable for continuous real-time measurements.

Invasive blood pressure (IBP) monitors penetrate the arterial wall and insert an arterial catheter into an artery of a subject to measure blood pressure. IBP monitors can provide continuous real-time measurements but are typically limited to hospital settings due to their invasive nature.

The subject matter claimed herein is not limited to implementations that solve any disadvantages or that operate only in environments such as those described above. Rather, this background is only provided to illustrate one example technology area where some implementations described herein may be practiced.

SUMMARY

This Summary is provided to introduce a selection of concepts in a simplified form that are further described below in the Detailed Description. This Summary is not intended to identify key features or essential characteristics of the claimed subject matter, nor is it intended to be used as an aid in determining the scope of the claimed subject matter.

In an example embodiment, a method to monitor blood pressure of a subject includes generating a first signal representing cardiac electrical activity of the subject using a first sensor of a wearable system. The method includes generating a second signal representing cardiac photonic activity of the subject using a second sensor of the wearable system. The method includes generating a third signal representing cardiac mechanical activity of the subject using a third sensor of the wearable system. The first, second, and third sensors are coupled to the subject. The method includes determining from the third signal a time period during which the first and second signals are likely clean. The method includes extracting one or more features from portions of two or more of the first, second, or third signals corresponding to the time period. The one or more extracted features include at least one of a pulse transit time (PTT), a pulse arrival time (PAT), or blood vessel elastics (BVE) features. The method includes determining a current blood pressure of the subject based on the one or more extracted features.

In another example embodiment, a wearable system configured to be coupled to a subject includes first, second, and third sensors, a processor device, and a non-transitory computer-readable storage medium. The first sensor detects cardiac electrical activity of the subject. The second sensor detects cardiac photonic activity of the subject. The third sensor detects cardiac mechanical activity of the subject. The processor device is communicatively coupled to each of the first, second, and third sensors. The non-transitory computer-readable storage medium has computer-executable instructions stored thereon that are executable by the processor device to perform or control performance of operations. The operations include generating a first signal representing cardiac electrical activity of the subject using the first sensor. The operations include generating a second signal representing cardiac photonic activity of the subject using the second sensor. The operations include generating a third signal representing cardiac mechanical activity of the subject using the third sensor. The operations include determining from the third signal a time period during which the first and second signals are likely clean. The operations include extracting one or more features from portions of two or more of the first, second, or third signals corresponding to the time period. The one or more extracted features include at least one of a PTT, a PAT, or BVE features. The operations include determining a current blood pressure of the subject based on the one or more extracted features.

In another example embodiment, a method to monitor blood pressure of a subject includes generating an electrocardiogram (ECG) signal over multiple cardiac cycles of the subject using an ECG sensor of a wearable system coupled to the subject. The method includes generating an optical signal over the cardiac cycles using an optical sensor of the wearable system. The ECG sensor and the optical sensor are integrated in the same wearable device. The method includes generating an accelerometer signal or an audio signal over the cardiac cycles using an accelerometer or acoustic sensor of the wearable system. The method includes determining from the accelerometer signal or the audio signal a time period during which the subject is stationary, the time period encompassing a subset of two or more of the cardiac cycles. The method includes extracting, for each cardiac cycle of the subset, one or more features from portions of two or more of the ECG, optical, or accelerometer/audio signals corresponding to the time period. The one or more extracted features for each cardiac cycle include at least one of a PTT, a PAT, or BVE features. The method includes one of: determining, for each cardiac cycle of the subset, instantaneous blood pressure of the subject based on the corresponding PTT, PAT, or BVE features extracted for the corresponding cardiac cycle; or determining average blood pressure of the subject based on an average of the PTTs, PATs, or BVE features across the subset of two or more of the cardiac cycles.

Additional features and advantages of the invention will be set forth in the description which follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF SOME EXAMPLE EMBODIMENTS

One noninvasive method of obtaining blood pressure measurements determines pulse transit time (PTT) from an electrocardiogram (ECG) signal measured at a first location of the subject's body (such as the subject's chest) and a photoplethysmography (PPG) signal measured at another location of the subject's body (such as the subject's fingertip) and then determines the blood pressure measurement from the PTT. In more detail, the heart ejects stroke volume (SV) with every beat. SV is the volume of blood pumped from the left ventricle per beat. When the heart ejects SV to the arteries, it takes a certain transit time, or PTT, until the blood pressure wave arrives in the periphery. The PTT indirectly depends on blood pressure—the higher the blood pressure, the faster (or smaller) the PTT. This circumstance can be used for the noninvasive detection of blood pressure changes. To obtain blood pressure absolute values, this method needs calibration with a blood pressure absolute value measurement from a different blood pressure monitor (such as a sphygmomanometer).

Figure 1:
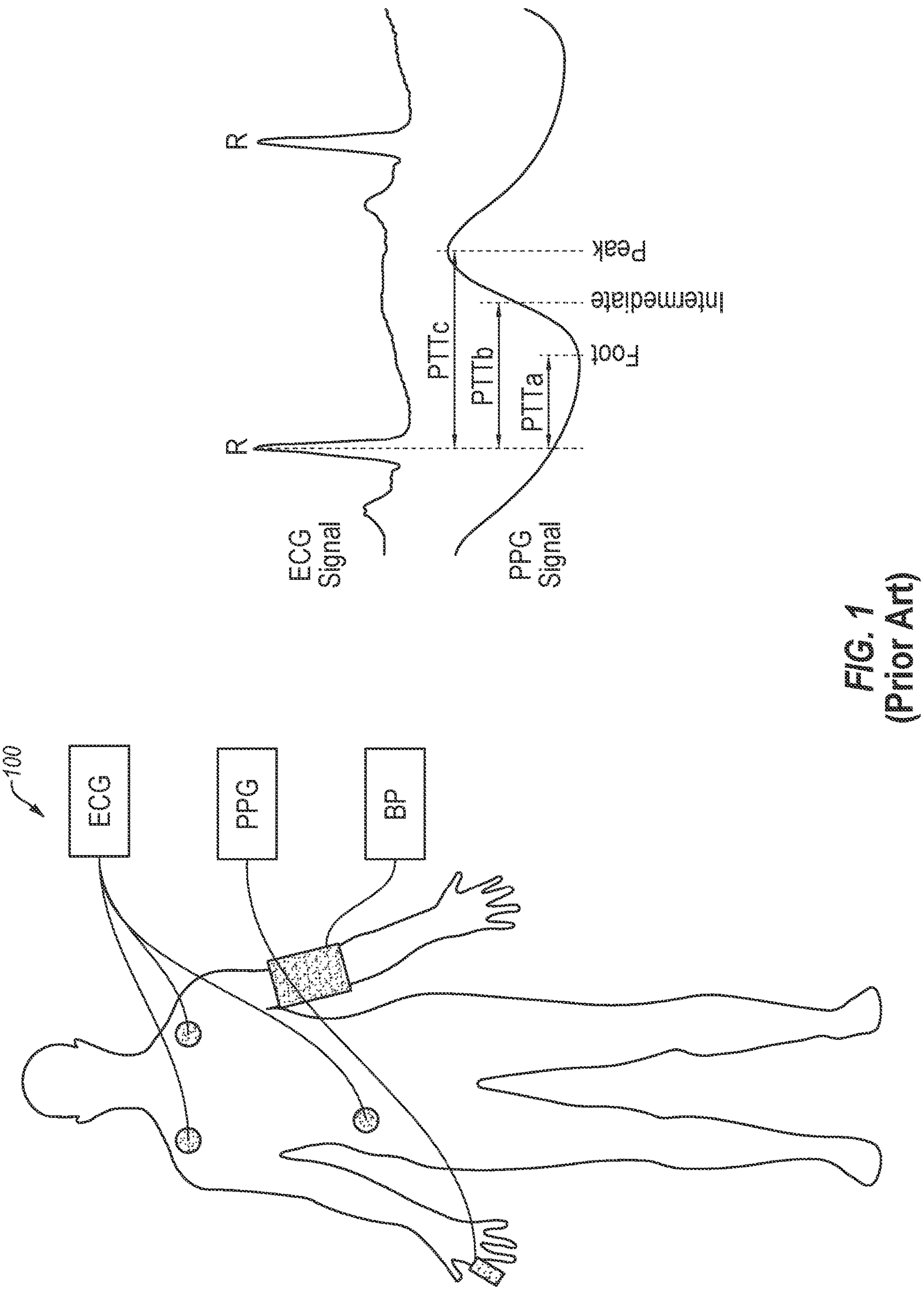
FIG. 1 (Prior Art)
FIG. 1 illustrates an example prior art system to implement a noninvasive method of obtaining blood pressure measurements of a subject.

FIG. 1 illustrates an example prior art system 100 to implement the foregoing noninvasive method of obtaining blood pressure measurements of a subject. As illustrated, the system 100 includes an ECG sensor, an optical sensor, and a blood pressure (BP) monitor. The ECG sensor includes three electrodes respectively coupled to three different locations of the subject's torso. The optical sensor is attached to the subject's fingertip and may include a single-wavelength or multi-wavelength optical sensor to derive blood volume changes and/or blood content measurements. In some embodiments, the optical sensor is a PPG sensor, a pulse oximeter, a peripheral oxygen saturation ($SpO_2$) sensor, or other optical sensor. The BP monitor is used for calibration and includes a cuff positioned on the subject's upper arm.

FIG. 1 further illustrates an example ECG signal and an example optical signal that may be generated by, respectively, the ECG sensor and the optical sensor of the system 100. With the ECG and optical signals time-aligned, one or more PTTs may be calculated as the delay between the R wave and a corresponding feature of the optical signal, such as the foot, the peak, or a particular intermediate magnitude between the foot and the peak. The PTT corresponding to the delay between the R wave and the foot of the optical signal is labeled PTTa in FIG. 1. The PTT corresponding to the delay between the R wave and one intermediate magnitude of the optical signal is labeled PTTb in FIG. 1. The PTT corresponding to the delay between the R wave and the peak of the optical signal is labeled PTTc in FIG. 1.

In the system 100 of FIG. 1, the subject must be connected, at a minimum, to both the ECG sensor and the discrete optical sensor (and additionally to the BP monitor during calibration) to obtain blood pressure measurements based on PTTs. Moreover, the subject may have to be stationary when measurements are taken by the ECG and optical sensors to reduce or eliminate noise in the ECG and optical signals. The nature of use and placement of the ECG and optical sensors on the subject in the system 100 may be uncomfortable, bothersome, may require that the user remain stationary while measurements are taken, and/or may interfere with or prevent the subject from performing normal activities unless the sensors are removed from the subject. The subject may forget to reconnect the sensors to the subject and/or the sensors may require recalibration after being removed from and reconnected to the subject. In view of the foregoing, the system 100 may be limited in its ability to obtain continuous blood pressure measurements from subjects unless the subjects consciously dedicate time to do so and pause engagement in other potentially interfering activities.

In comparison, some embodiments herein relate to a wearable system that may remain coupled to a subject (e.g., directly to the subject's skin and/or on the subject's torso or other location) for hours, days, or even weeks at a time. The wearable system may include multiple collocated sensors, e.g., sensors integrated into the same wearable system and/or where the sensors are not more than 2 inches from each other. Alternatively or additionally, the sensors of the wearable system may be spaced apart from each other in separate locations on the subject while implementing a wireless signaling scheme (e.g., over Bluetooth) for synchronization/time alignment with a precision of 1 millisecond (ms) or less. For example, one or more of the sensors of the system may be on the subject's torso while one or more other sensors of the system may be on the subject's finger, hand, arm, or other location. In these and other examples, the sensors may include, e.g., an ECG sensor, an optical sensor, an accelerometer, an acoustic sensor, or other suitable sensors, all configured to generate signals representing cardiac activity of the subject. For example, the ECG sensor may generate an ECG signal representing cardiac electrical activity, the optical sensor may generate an optical signal representing cardiac photonic activity, the accelerometer may generate an accelerometer signal representing cardiac mechanical activity and/or motion/movement of the subject, and/or the acoustic sensor may generate an audio signal representing cardiac mechanical activity. The accelerometer and/or acoustic sensor may detect time periods when the various signals are likely to be clean, such as time periods when the subject is stationary. One or more features, including at least one of PTT, pulse arrival time (PAT), or blood vessel elastics (BVE) features, and/or one or more additional features may be extracted from portions of the various signals corresponding to time periods when the signals are likely to be clean and/or time periods when the subject is stationary. Finally, blood pressure, e.g., mean arterial blood pressure (MAP), systolic blood pressure (SBP), and/or diastolic blood pressure (DBP), may be estimated from the extracted features. In some embodiments, the wearable system may be calibrated with one or more blood pressure absolute value measurements from a sphygmomanometer or other blood pressure monitor to generate blood pressure absolute value measurements using the wearable system.

Further, body position may influence blood pressure. Accordingly, in some embodiments body position may be detected, e.g., by the accelerometer and/or other sensor(s), during calibration and successive measurements and may be used as an input to the blood pressure estimates and/or calibration. Alternatively or additionally, a respiratory rate signal may be derived from the EKG signal and/or the accelerometer signal. Some embodiments may determine from the respiratory rate signal respiratory rate intervals, inspiratory time intervals, and/or expiratory time intervals. One or more of the respiratory rate signal, respiratory rate intervals, inspiratory time intervals, and/or expiratory time intervals may be used as an input to blood pressure estimation. In some embodiments, oxygen saturation, e.g., $SpO_2$ output from the optical sensor, may be used as an input to blood pressure estimation.

Reference will now be made to the drawings to describe various aspects of example embodiments of the invention. It is to be understood that the drawings are diagrammatic and schematic representations of such example embodiments, and are not limiting of the present invention, nor are they necessarily drawn to scale.

Figure 2:
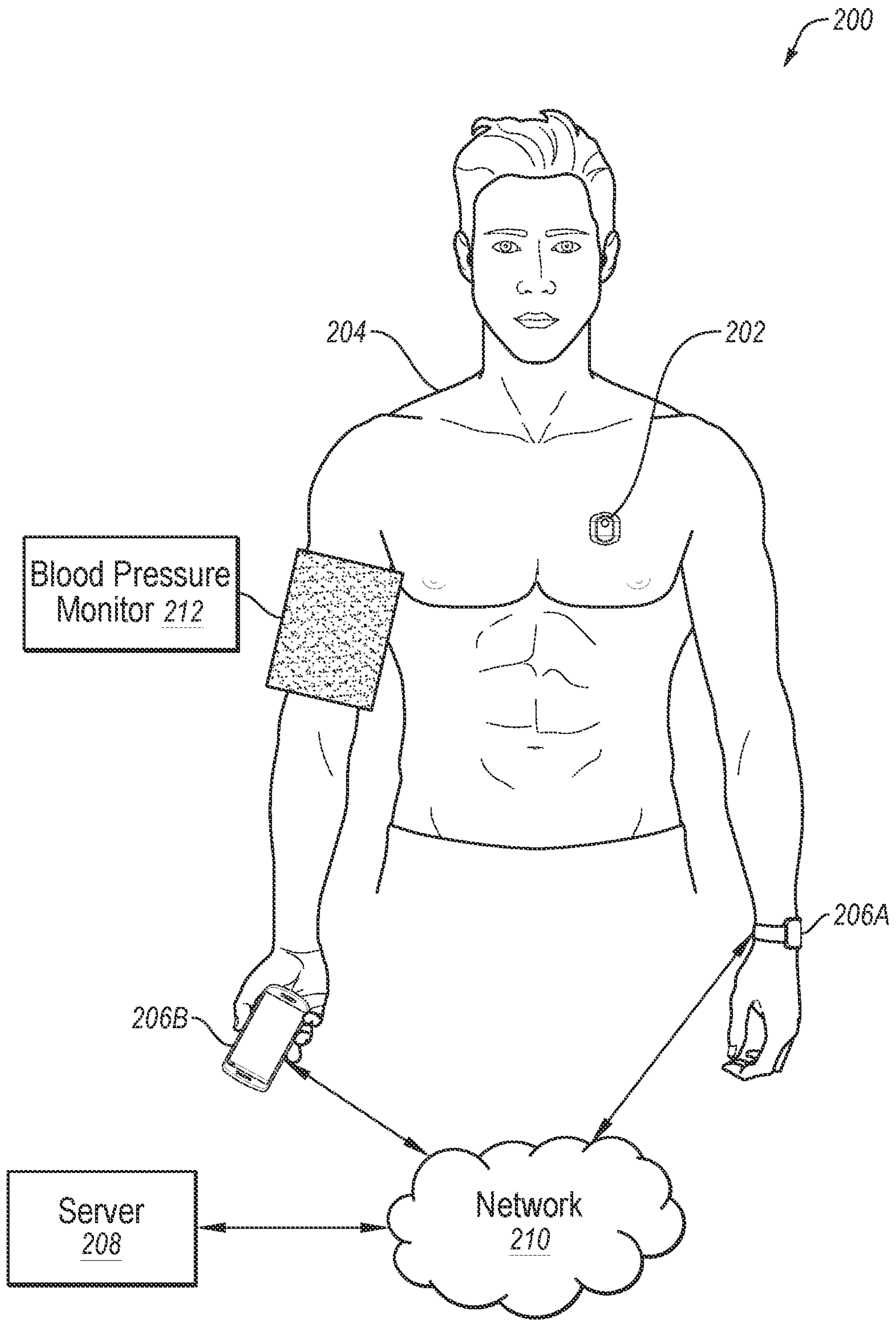
FIG. 2 illustrates an example operating environment that includes a wearable system to monitor blood pressure.

FIG. 2 illustrates an example operating environment 200 (hereinafter "environment 200") that includes a wearable system 202 (hereinafter "system 202") to monitor blood pressure, arranged in accordance with at least one embodiment described herein. The environment 200 may further include a subject 204 and one or more personal electronic devices 206A, 206B (hereinafter collectively "personal electronic devices 206" or generically "personal electronic device 206"). The environment 200 may additionally include a server 208, a network 210, and/or a blood pressure monitor 212.

The system 202 may generally be coupled to the subject 204 to monitor and/or measure one or more biological parameters of the subject 204, such as cardiac activity (e.g., electrical, photonic, acoustic, or mechanical), respiratory activity (e.g., respiratory rate, inspiratory time, expiratory time), body position, blood oxygen, skin temperature, body temperature, or others. The system 202 is illustrated in FIG. 2 as being coupled to skin of the subject 202 and in particular on the torso of the subject 202, but more generally the system 202 may be coupled to the subject 202 at any desired location. An example implementation of the system 202 may include multiple integrated sensors. Another example implementation of the system 202 may include two or more separate sensors (e.g., separate from each other) with precise (e.g., 1 ms or less) time alignment via wireless signaling. In these and other implementations, the sensors generate, for instance, ECG signals or data, optical signals or data, accelerometer signals or data, audio signals or data, temperature signals or data, respiratory signals or data, or other measurement signals or data. The signals or data generated by the system 202 and/or its sensors may be referred to generally as measurement data. The system 202 may provide portions or all of the measurement data and/or data derived from the measurement data, to the personal electronic devices 206 and/or the server 208. In some embodiments, the system 202 implements a light-weight machine-learning (ML) model, e.g., a linear regression model, a support vector machine model, a random forest model, a data clustering model, an XG boost model, and/or other light-weight ML model, to generate blood pressure measurements (e.g., MAP, SBP, and/or DBP) based on one or more features extracted from ECG, PPG, accelerometer, audio, and/or other signals. Alternatively or additionally, the extracted features and/or the raw data of the various sensors of the system 202 may be selectively sent to the server 208 for more comprehensive and less resource-constrained regression algorithms, ML models, deep learning models, statistical models, or any combination thereof. Examples of the foregoing that may be implemented herein include convolutional neural network (CNN), long short-term memory (LSTM), and recurrent neural network (RNN).

The personal electronic devices 206 may each include a desktop computer, a laptop computer, a tablet computer, a smartphone, a wearable electronic device (e.g., smart watch, activity tracker, headphones, ear buds, etc.), or other personal electronic device. In the illustrated example, the personal electronic device 206A is a smart watch and the personal electronic device 206B is a smartphone. In some embodiments, the personal electronic devices 206 may collect measurement data from the system 202 for use and/or analysis on the personal electronic devices 206.

Alternatively or additionally, the measurement data generated by the system 202 and/or data derived therefrom may be uploaded, e.g., periodically, by the system 202 to the remote server 208. In some embodiments, one or more of the personal electronic devices 206 or another device may act as a hub that collects measurement data or data derived therefrom from the system 202 and/or other personal electronic devices 206 and uploads the measurement data or data derived therefrom to the server 208. For example, the hub may collect data over a local communication scheme (WI-FI, BLUETOOTH, near-field communications (NFC), etc.) and may transmit the data to the server 208. In some embodiments, the hub may collect the data and periodically provide the data to the server 208, such as once per week. An example hub and associated methods and devices are disclosed in U.S. Pat. No. 10,743,091, which is incorporated herein by reference.

The server 208 may include a collection of computing resources available in the cloud and/or a discrete server computer. The server 208 may be configured to receive measurement data and/or data derived from measurement data from one or more of the personal electronic devices 206 and/or from the system 202. Alternatively or additionally, the server 208 may be configured to receive from the system 202 (e.g., directly or indirectly via a hub device) relatively small portions of the measurement data, or even larger portions or all of the measurement data. The server 208 may use and/or analyze the data to, e.g., generate continuous blood pressure measurements for at least some time periods in a day. Alternatively or additionally, the server 208 may store the measurement data in an account of the subject 204 and make the measurement data or data derived therefrom available to the subject 204, a healthcare provider, or other individuals, e.g., as authorized by the subject 204 e.g., via an online portal.

The network 210 may include one or more wide area networks (WANs) and/or local area networks (LANs) that enable the system 202, the personal electronic devices 206, and/or the server 208 to communicate with each other. In some embodiments, the network 210 includes the Internet, including a global internetwork formed by logical and physical connections between multiple WANs and/or LANs. Alternately or additionally, the network 210 may include one or more cellular radio frequency (RF) networks and/or one or more wired and/or wireless networks such as 802.xx networks, BLUETOOTH access points, wireless access points, IP-based networks, or other suitable networks. The network 210 may also include servers that enable one type of network to interface with another type of network.

The blood pressure monitor 212 may be a manual blood pressure monitor, a digital blood pressure monitor, or other blood pressure monitor configured to generate blood pressure absolute value measurements. Manual blood pressure monitors may generally include a sphygmomanometer (including a manually or electronically inflatable/deflatable cuff and a pressure sensor (e.g., aneroid or mercury column)), such as a mercury or aneroid sphygmomanometer, used together with a stethoscope operated by a trained practitioner. Digital blood pressure monitors may generally include a sphygmomanometer and an electronic pressure sensor.

The blood pressure absolute value measurements generated by the blood pressure monitor 212 may be used by the system 202 and/or the server 208 to calibrate the system 202 for generating blood pressure measurements based on optical signals and one or more other measurement signals generated by the system 202. In some embodiments, the blood pressure monitor 212 is used occasionally but not continuously to generate occasional blood pressure absolute value measurements for occasional calibration/recalibration of the system 202. As used herein, "occasional" and its variants refers to non-continuous usage in which the blood pressure monitor 212 is not attached to the subject 204 at all times and is only attached to the subject 204 to take one or more measurements before being removed until the next occasional measurement. Occasional measurements may include measurements generated according to a predefined schedule, periodically (e.g., once every other day, every three days, every four days, every week, etc.), randomly, or in some other manner.

Figure 3:
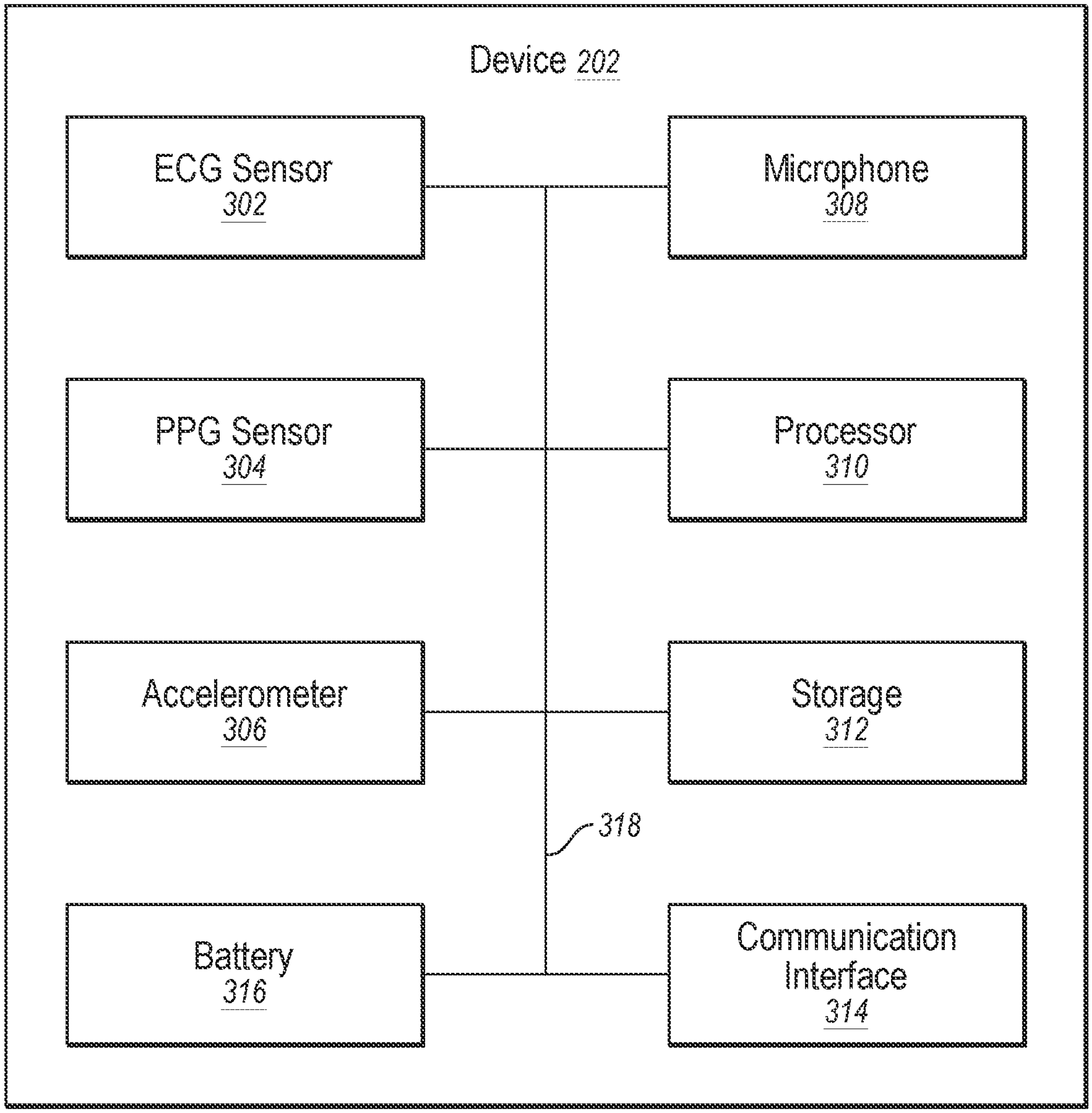
FIG. 3 illustrates an example implementation of the wearable system of FIG. 2.

FIG. 3 illustrates an example implementation of the system 202 of FIG. 2, arranged in accordance with at least one embodiment described herein. In general, the system 202 includes multiple sensors, such as an ECG sensor 302, an optical sensor 304, and at least one of an accelerometer 306 (or other movement sensor) or a microphone 308 (or other acoustic sensor) to detect movement of a subject's heart and/or movement of the subject. The system 202 may further include a processor 310, storage 312, a communication interface 314, a battery 316, a communication bus 318, and/or other sensors, components, or devices.

The ECG sensor 302 may be configured to detect cardiac electrical activity of a subject. For example, the ECG sensor 302 may detect electrical signals generated by the SA node of the subject's heart and may generate an ECG signal that represents or corresponds to the detected electrical signals.

The optical sensor 304 may be configured to detect cardiac photonic activity of the subject. For example, the optical sensor 304 may detect changes in blood volume during each cardiac cycle based on changes in light absorption caused by changes in blood volume at a given location of the subject's body during each cardiac cycle. In some embodiments, the optical sensor 304 is or includes a multi-channel optical sensor. A multi-channel optical sensor may detect absorption of multiple different (although potentially overlapping) wavelength ranges, or channels, of light and generate an optical signal based on two or more of the detected channels. An optical signal generated based on multiple channels by a multi-channel optical sensor may be referred to herein as a multi-channel optical signal. An example of a multi-channel optical sensor that may be implemented herein as the optical sensor 304 in some embodiments is described in U.S. Pat. No. 10,485,463 which is incorporated herein by reference in its entirety.

The accelerometer 306 may generally be configured to detect movement of the subject and/or movement of a portion of the subject to which the accelerometer is coupled and to generate an accelerometer signal that represents or corresponds to the detected movement. In some embodiments, when placed on the subject's torso, the accelerometer 306 may capture movement of the subject as a whole and/or movement (e.g., beating) of the subject's heart by virtue of the movement of the heart causing small but detectable movements of the subject's chest wall.

The microphone 308 may generally be used to record sound that may or may not be audible to the subject and may be oriented to face the skin of the subject. For example, the microphone 308 may be used to record the sound of the subject's cardiac cycle from which, e.g., the subject's heart rate may be derived. While the term microphone is used, more generally the system 202 may include any type of acoustic sensor that may be configured to detect sound waves and convert them into a readable signal such as an electronic signal. For example, a phonocardiogram, a piezoelectric transducer, a condenser microphone, a moving-coil microphone, a fiber optic microphone, a Micro-Electrical-Mechanical System (MEMS) microphone, etc. or any other transducer may be used as or in addition to the microphone 308.

Accordingly, in some embodiments, the accelerometer 306 and/or the microphone 308 may be configured to detect cardiac mechanical activity of the subject. As already indicated, for instance, the accelerometer 306 may detect movement of the subject's torso corresponding to movement of the subject's heart during each cardiac cycle. Alternatively or additionally, the microphone 308 may detect sounds corresponding to movement of the subject's heart during each cardiac cycle. More generally, and instead of or in addition to the accelerometer 306 and/or the microphone 308, the system 202 may include any suitable sensor couplable to a subject's torso or other location to generate a signal representing detected motion or mechanical displacement where one or more physiological parameters and/or patient activity level may be determined or derived from the signal.

In these and other embodiments, one or both of the accelerometer 306 or the microphone 308 may detect periods of time when the subject is stationary and/or periods of time when signals generated by the ECG sensor 302, the optical sensor 304, the accelerometer 306, and/or the microphone 308 are likely clean. For example, the signal generated by the accelerometer 306 and/or the microphone 308 may have a certain pattern, signature, or fingerprint and/or may have peak-to-valley excursions less than a threshold, or satisfy one or more other or additional criteria, when the subject is stationary, which may facilitate identification of periods of time when the subject is stationary. In an example, the processor 310 may analyze the signal generated by the accelerometer 306 or microphone 308 and when the signal exhibits the pattern, signature, or fingerprint and/or has peak-to-valley excursions less than the threshold, the processor 310 may determine that the subject is stationary until the signal generated by the accelerometer 306 or microphone 308 no longer exhibits the pattern, signature, or fingerprint and/or has peak-to-valley excursions greater than the threshold. As another example, the signal generated by the accelerometer 306 and/or the microphone 308 may have a certain pattern (such as when walking), signature, fingerprint, or other characteristic(s) or satisfy one or more other or additional criteria when the subject is moving, which may facilitate identification of periods of time when the subject is stationary (e.g., the periods of time when the signal does not exhibit the pattern(s) associated with movement). In this example, the processor 310 may analyze the signal generated by the accelerometer 306 or microphone 308 and when the signal exhibits the pattern, signature, or fingerprint the processor 310 may determine that the subject is moving until the signal generated by the accelerometer 306 or microphone 308 no longer exhibits the pattern, signature, or fingerprint. In these and other examples, the processor 310 may record the start and end time of any given period of time when the subject is stationary, time-align signals generated by the ECG sensor 302, the optical sensor 304, or other sensors of the system 202, save portions of the signals from the start time to the end time in the storage 312, generate and/or save data derived from the portions in the storage 312, upload the portions and/or the data derived therefrom to the cloud (e.g., to the server 208), or the like or any combination thereof. Alternatively or additionally, the processor 310 may extract one or more features from one or more of the portions and determine a blood pressure of the subject based on the extracted features.

Insofar as movement of the subject may insert noise in signals generated by the ECG sensor 302, the optical sensor 304, and/or other sensors of the system 202, periods of time when the signals of the ECG sensor 302, the optical sensor 304, and/or other sensors of the system 202 are likely clean may be determined based on the movement of the subject as detected by the accelerometer 306 and/or the microphone 308. For example, periods of time when the signals of the ECG sensor 302, the optical sensor 304, and/or other sensors of the system 202 are likely clean may be determined as the same periods of time as those when the subject is stationary and/or within the periods of time when the subject is stationary.

Although not illustrated in FIG. 3, the system 202 may include one or more other sensors, such as a temperature sensor, a respiratory sensor, a gyrometer sensor, an accelerometer sensor, an optical spectrometer sensor, an electrochemical sensor, an oxygen saturation sensor, an electrodermal activity (EDA) sensor, a volatile organic compound (VOC) sensor, an optical sensor, a spectrometer, or any combination thereof. A temperature sensor may be used to detect temperatures associated with a subject, such as skin temperature and/or core body temperature. A respiratory sensor may be used to detect respiration of the subject. A gyrometer or accelerometer sensor may be used to measure angular velocity of at least a portion of the subject, such as the chest of the subject. An oxygen saturation sensor may be used to record blood oxygenation of the subject. An EDA sensor may be used to measure EDA of the skin of the subject. A VOC detector may be used to detect various organic molecules that may be coming off of the subject or that may be in the subject's sweat. An optical sensor (the optical sensor 304 or other optical sensor of the system 202) may be used to monitor or detect changes in color, such as changes in skin coloration of the subject. A spectrometer may measure electromagnetic (EM) radiation and may be configured to detect variations in reflected EM radiation. For example, such a sensor may detect changes in color in a molecule exposed to multi-spectral light (e.g., white light), and/or may detect other changes in reflected EM radiation outside of the visible spectrum (e.g., interaction with ultraviolet rays, etc.).

The processor 310 may include any device or component configured to monitor and/or control operation of the system 202. For example, the processor 310 may retrieve instructions from the storage 312 and execute those instructions. As another example, the processor 310 may read the signals and/or measurement data generated by sensors (e.g., the ECG sensor 302, the optical sensor 304, the accelerometer 306, the microphone 308, and/or other sensors) and may store the readings in the storage 312 or instruct the communication interface 314 to send the readings to another electronic device, such as the server 208 of FIG. 2. In some embodiments, the processor 310 may include an arithmetic logic unit, a microprocessor, a general-purpose controller, or some other processor or array of processors, to perform or control performance of operations as described herein. The processor 310 may be configured to process data signals and may include various computing architectures including a complex instruction set computer (CISC) architecture, a reduced instruction set computer (RISC) architecture, or an architecture implementing a combination of instruction sets. Although illustrated as a single processor 310, multiple processor devices may be included and other processors and physical configurations may be possible. The processor 310 may be configured to process any suitable number format including, but not limited to two's compliment numbers, integers, fixed binary point numbers, and/or floating point numbers, etc. all of which may be signed or unsigned. In some embodiments, the processor 310 may perform processing on the readings from the sensors prior to storing and/or communicating the readings. For example, raw analog data signals generated by the ECG sensor 302, the optical sensor 304, the accelerometer 306, the microphone 308, and/or other sensors of the system 202 may be down-sampled, may be converted to digital data signals, and/or may be processed in some other manner.

The storage 312 may include non-transitory computer-readable storage media or one or more non-transitory computer-readable storage mediums for carrying or having computer-executable instructions or data structures stored thereon. Such non-transitory computer-readable storage media may be any available non-transitory media that may be accessed by a general-purpose or special-purpose computer, such as the processor 310. By way of example such non-transitory computer-readable storage media may include Random Access Memory (RAM), Read-Only Memory (ROM), Electrically Erasable Programmable Read-Only Memory (EEPROM), flash memory devices (e.g., solid state memory devices), or any other non-transitory storage medium which may be used to carry or store desired program code in the form of computer-executable instructions or data structures and which may be accessed by a general-purpose or special-purpose computer. In some embodiments, the storage 312 may alternatively or additionally include volatile memory, such as a dynamic random access memory (DRAM) device, a static random access memory (SRAM) device, or the like. Combinations of the above may also be included within the scope of non-transitory computer-readable storage media. Computer-executable instructions may include, for example, instructions and data that when executed by the processor 310 cause the processor 310 to perform or control performance of a certain operation or group of operations. In some embodiments, the storage 312 may store the data signals, e.g., measurement data, generated by the ECG sensor 304, the temperature sensor 310, the respiratory sensor 312, the accelerometer 314, the microphone 316, and/or other sensors of the system 202 and/or data derived therefrom.

The communication interface 314 may include any device or component that facilitates communication with a remote device, such as any of the personal electronic devices 206 of the subject 204, the server 208, or any other electronic device. For example, the communication interface 314 may include an RF antenna, an infrared (IR) receiver, a WI-FI chip, a BLUETOOTH chip, a cellular chip, a near-field communication (NFC) chip, or any other communication interface.

The battery 316 may include any device or component configured to provide power to the system 202 and/or the components thereof. For example, the battery 316 may include a rechargeable battery, a disposable battery, etc. In some embodiments, the system 202 may include circuitry, electrical wires, etc. to provide power from the battery 316 to the other components of the system 202. In some embodiments, the battery 316 may include sufficient capacity such that the system 202 may operate for days, weeks, or months without having the battery changed or recharged. For example, the system 202 may be configured to operate for at least two months without having the battery 316 charged or replaced.

The communication bus 318 may include any connections, lines, wires, or other components facilitating communication between the various components of the system 202. The communication bus 318 may include one or more hardware components and may communicate using one or more protocols. Additionally or alternatively, the communication bus 318 may include wire connections between the components.

In some embodiments, the system 202 may operate in a similar or comparable manner to the embodiments described in U.S. application Ser. No. 17/349,166 filed on Jun. 16, 2021 and/or U.S. Pat. No. 11,172,909, both of which are hereby incorporated by reference.

FIG. 3 illustrates the system 202 as an integrated device in which all components are integrated in the same device. In other embodiments, two or more of the components of the system 202 may be distributed from each other. For example, the ECG sensor 302 (potentially with a processor, battery, storage, and/or other components) may be implemented in one device while the optical sensor 304 (potentially with another processor, battery, storage, and/or other components), the accelerometer 306 (potentially with still another processor, battery, storage, and/or other components), and/or the microphone 308 (potentially with still another processor, battery, storage, and/or other components) may be implemented in separate devices that collectively make up the system 202. In these and other embodiments, the components implemented in a given device may communicate with or be coupled to each other via a communication bus such as the communication bus 318, while each device may communicate with other devices of the system 202 through a corresponding communication interface, such as the communication interface 314. For example, each of the devices may include a wireless communication interface such as a wireless (e.g., WiFi, Bluetooth, ZigBee) chip. The devices may be time-aligned and/or may time-align their sensor signals to a precision of 1 ms or less via wireless signaling. The sensor signals generated at each of the devices may be collected at one or more of the devices and/or may be transmitted elsewhere, e.g., to the server 208 of FIG. 2.

Figure 4A:
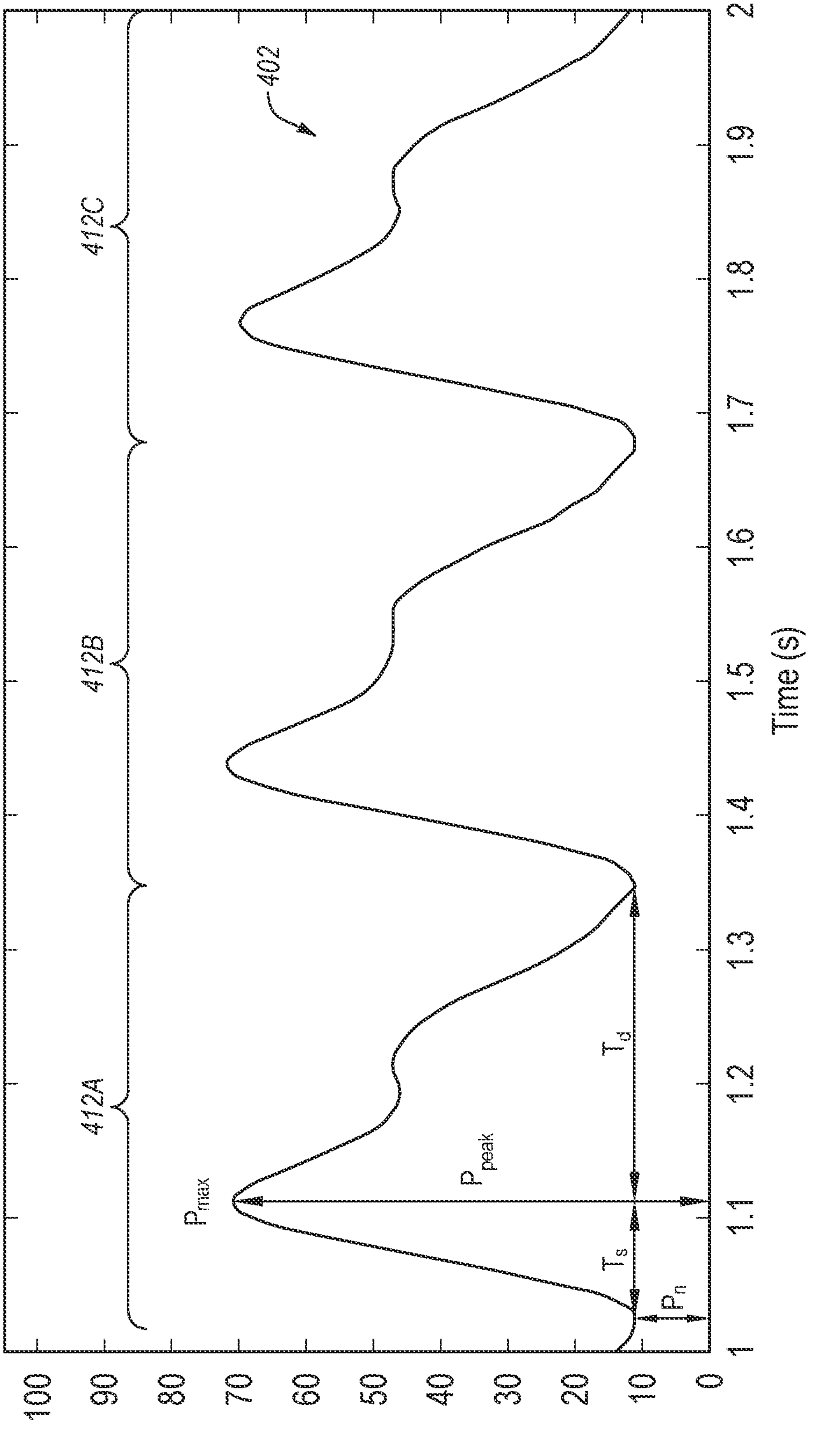
FIGS. 4A-4C illustrate portions of various measurement signals and features that may be extracted therefrom.
Figure 4B:
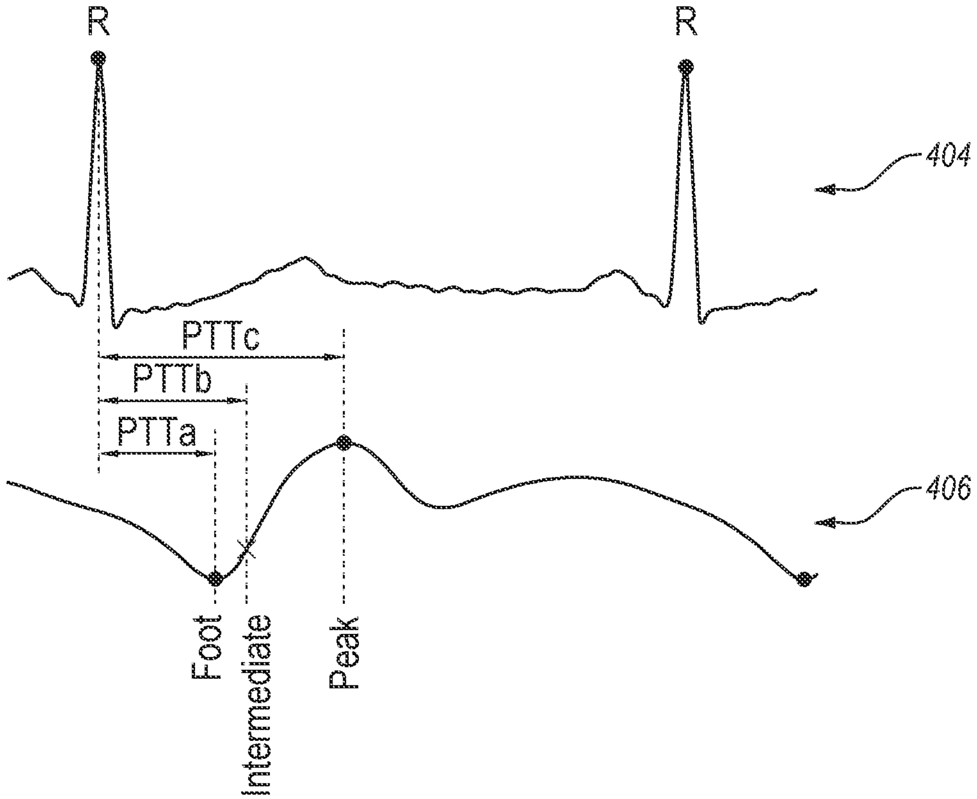
Figure 4C:
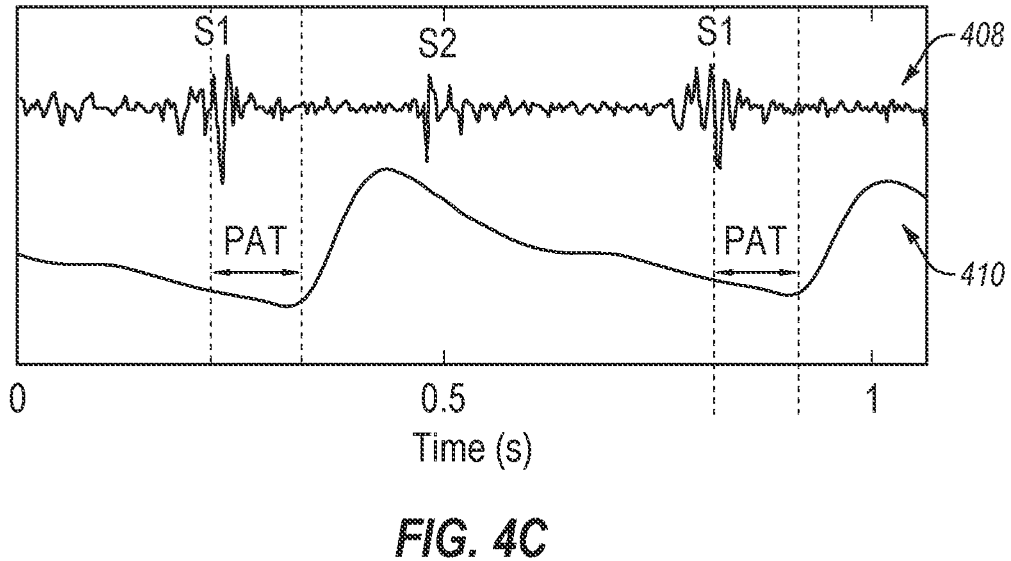

FIGS. 4A-4C illustrate portions of various measurement signals 402, 404, 406, 408, 410 and features that may be extracted therefrom, arranged in accordance with at least one embodiment described herein. In more detail, FIG. 4A includes an optical signal 402 that may be generated by a pulse oximeter or other optical sensor, such as the optical sensor 304. FIG. 4B includes an ECG signal 404 that may be generated by an ECG sensor, such as the ECG sensor 302, and an optical signal 406 that may be generated by a pulse oximeter or other optical sensor, such as the optical sensor 304. FIG. 4C includes an accelerometer signal or audio signal 408 (hereinafter "accelerometer signal 408" for simplicity) that may be generated by an accelerometer or acoustic sensor, such as the accelerometer 306 or microphone 308, and an optical signal 410 that may be generated by a pulse oximeter or other optical sensor, such as the optical sensor 304. In each of FIGS. 4B and 4C, the optical signal 406, 410 is time-aligned with, respectively, the ECG signal 404 or the accelerometer signal 408. The various measurement signals 402, 404, 406, 408, 410 are relatively clean and may have been generated at a time period when likely to be clean, e.g., when the subject from which the measurement signals 402, 404, 406, 408, 410 are taken was stationary so as to minimize, or at least reduce, signal noise compared to when the subject is moving.

FIGS. 4A-4C additionally illustrate various features that may be extracted from the portions of the measurement signals 402, 404, 406, 408, 410. Referring to FIG. 4A, the optical signal 402 of FIG. 4A includes three distinct pulse waves 412A, 412B, 412C (hereinafter collectively "pulse waves 412" or generically "pulse wave 412"), each corresponding to a different one of three consecutive cardiac cycles of a subject. The optical signal 402, and other optical signals herein, is a measure of optical absorption of an area of the subject, the optical absorption changing as a function of time as blood volume in the area changes according to the cardiac cycle. Each pulse wave 412 includes various features, one or more of which may be extracted and used to determine blood pressure of the subject. Labels of the various pulse wave features are applied in FIG. 4A only to the pulse wave 412A for simplicity. Each pulse wave 412 includes a peak that occurs at a time $P_{max}$ with a pulse wave amplitude $P_{peak}$ and a nadir that occurs at a time $P_{nadir}$. Each pulse wave 412 includes a systolic upstroke interval ($T_s$) or rise time (RT) calculated as the time interval from $P_{nadir}$ of the pulse wave 412 to $P_{max}$ of the pulse wave 412. $T_s$ or RT may be associated with contractile force and left ventricular function of the subject. Each pulse wave 412 includes a diastolic interval $T_d$ or descent time (DT) calculated as the time interval from $P_{max}$ of the pulse wave 412 to $P_{nadir}$ of the subsequent pulse wave 412. $T_d$ or DT may be associated with ventricular diastole of the subject. The features of optical signals such as the optical signal 402 that may be extracted according to some embodiments herein may include one or more of $P_{max}$, $P_{peak}$, $P_{nadir}$, $T_s$ (or RT), $T_d$ (or DT), and/or other features.

Referring to FIG. 4B, various PTTs are illustrated that are examples of extractable features that may be extracted from time-aligned ECG and optical signals, such as the ECG signal 404 and the optical signal 406 to use in determining blood pressure. The ECG signal 404 includes two R waves, each corresponding to a different one of two consecutive cardiac cycles of the subject. Each PTT in FIG. 4B may be extracted by calculating a delay between an R wave of the ECG signal 402 and a corresponding feature of the pulse wave of the optical signal 404, such as a foot or nadir of the pulse wave, a peak or $P_{max}$ of the pulse wave, or an intermediate magnitude between the foot and the peak. The intermediate magnitude may be any desired intermediate magnitude. The PTT corresponding to the delay between the R wave and the foot of the pulse wave of the optical signal is labeled PTTa in FIG. 4B. The PTT corresponding to the delay between the R wave and one intermediate magnitude of the pulse wave of the optical signal is labeled PTTb in FIG. 4B. The PTT corresponding to the delay between the R wave and the peak of the pulse wave of the optical signal is labeled PTTc in FIG. 4B.

Referring to FIG. 4C, two consecutive PATs are illustrated that are examples of extractable features that may be extracted from time-aligned accelerometer/audio and optical signals, such as the accelerometer signal 408 and the optical signal 410, to use in determining blood pressure. Accelerometer signals or audio signals generated by an accelerometer (or other motion sensor) or a microphone (or other acoustic sensor), such as the accelerometer signal 408, may have one or more features for each cardiac cycle that result from vibrations created by the closure of the subject's heart valves. In this respect, the accelerometer signals or audio signals may be the same as or similar to phonocardiograms. In the illustrated example, the accelerometer signal 408 includes, for each cardiac cycle, an S1 feature detected as a vibration produced when the atrioventricular valves (tricuspid and mitral) close at the beginning of systole and an S2 feature detection as a vibration produced when the aortic valve and pulmonary valve (semilunar valves) close at the end of systole. Other features may be present in accelerometer or audio signals generated by accelerometers or acoustic sensors near a subject's heart depending on the subject; for example, various heart murmurs (aortic stenosis, mitral regurgitation, aortic regurgitation, mitral stenosis, patent ductus arteriosus, or the like) may manifest different features in a corresponding accelerometer or audio signal. The PATs in FIG. 4C may be extracted by calculating a delay between an S1 feature and a corresponding feature of the pulse wave of the optical signal 410, such as a foot or nadir of the pulse wave as illustrated in FIG. 4C, or between the S1 feature and some other feature (e.g., peak, intermediate magnitude) of the optical signal 410.

FIG. 4C depicts two PATs calculated in the same manner (e.g., delay between S1 feature of accelerometer signal 408 and foot or nadir of optical signal 410) for consecutive cardiac cycles. Each PAT individually or in combination with one or more other extracted features from a corresponding cardiac cycle may be used to determine an instantaneous blood pressure measurement for the cardiac cycle. Alternatively or additionally, multiple PATs from multiple cardiac cycles may be averaged or otherwise combined across multiple cardiac cycles (e.g., a mean PAT) to determine an average or other (e.g., mean) blood pressure measurement across the cardiac cycles. Alternatively or additionally, one or more other features may be averaged or otherwise combined (e.g., mean) across multiple cardiac cycles and the average or other (e.g., mean) one or more features may be used together with the average or other (e.g., mean) blood pressure measurement to determine the average or other (e.g., mean) blood pressure measurement across the cardiac cycles.

The foregoing are examples of features that may be extracted from ECG signals, optical signals, accelerometer signals, audio signals, and/or other signals for use in determining blood pressure. Alternatively or additionally, the one or more features that may be extracted may include BVE features such as a pressure constant k (PK) that is related to a total peripheral resistance (TPR) of a circulatory system of the subject; a photoplethysmography area (PA) that is associated with the TPR and changes in blood vessel tension of the subject (e.g., total area under a PPG pulse wave from its foot or nadir to the foot or nadir of the next pulse wave); the systolic upstroke time/interval ($T_s$ or RT) that reflects the heart contraction and left ventricular function; the diastolic interval or descent time ($T_d$ or DT) which is related to ventricular diastole; a pulsatile hetero height (PHH) that is associated with a magnitude of cardiac output of the subject; the pulse wave amplitude $P_{peak}$; and/or other features. Additional details regarding example features that may be extracted from ECG signals, optical signals, accelerometer signals, audio signals, and/or other signals that may be generated by a wearable system such as the system 202, as well as example methods of determining blood pressure from one or more such extracted features and/or covariates (e.g., heart rate) that may be implemented herein, are disclosed in the following articles, each of which is incorporated herein by reference in its entirety: Feng, Jingjie & Huang, Zhongyi & Congcong, Zhou & Ye, Xuesong (2018), Study of continuous blood pressure estimation based on pulse transit time, heart rate and photoplethysmography-derived hemodynamic covariates, Australasian Physical & Engineering Sciences in Medicine. 41. 10.1007/s13246-018-0637-8; Chen M W, Kobayashi T, Ichikawa S, Takeuchi Y, Togawa T (2000), Continuous estimation of systolic blood pressure using the pulse arrival time and intermittent calibration, Med Biol Eng Comput 38(5):569-574; Escobar B, Torres R (2014), Feasibility of non-invasive blood pressure estimation based on pulse arrival time: a MIMIC database study, In: Computing in cardiology 2014, 7-10 Sep. 2014, pp. 1113-1116; Poon C C Y, Zhang Y T (2005), Cuff-less and noninvasive measurements of arterial blood pressure by pulse transit time, In: 2005 IEEE Engineering in Medicine and Biology 27th annual conference, 17-18 Jan. 2006, pp. 5877-5880); Zheng Y L, Yan B P, Zhang Y T, Poon C C Y (2014), An armband wearable device for overnight and cuff-less blood pressure measurement, IEEE Trans Biomed Eng 61(7):2179-2186. Gesche H, Grosskurth D, Kuchler G, Patzak A (2012), Continuous blood pressure measurement by using the pulse transit time: comparison to a cuff-based method. Eur J Appl Physiol 112(1):309-315.

In some embodiments, signal quality of the ECG signals, optical signals, accelerometer signals, audio signals, and/or other signals generated and used herein may be improved by using only those portions of the signals that are clean or likely clean, such as portions generated during time periods when the subject is stationary (e.g., as indicated by an accelerometer signal and/or audio signal). Alternatively or additionally, features such as PTT and/or PAT that are extracted from the signals may be averaged over multiple cardiac cycles, e.g., for some or all of the portions of the signals that are clean or likely clean.

Figure 5:
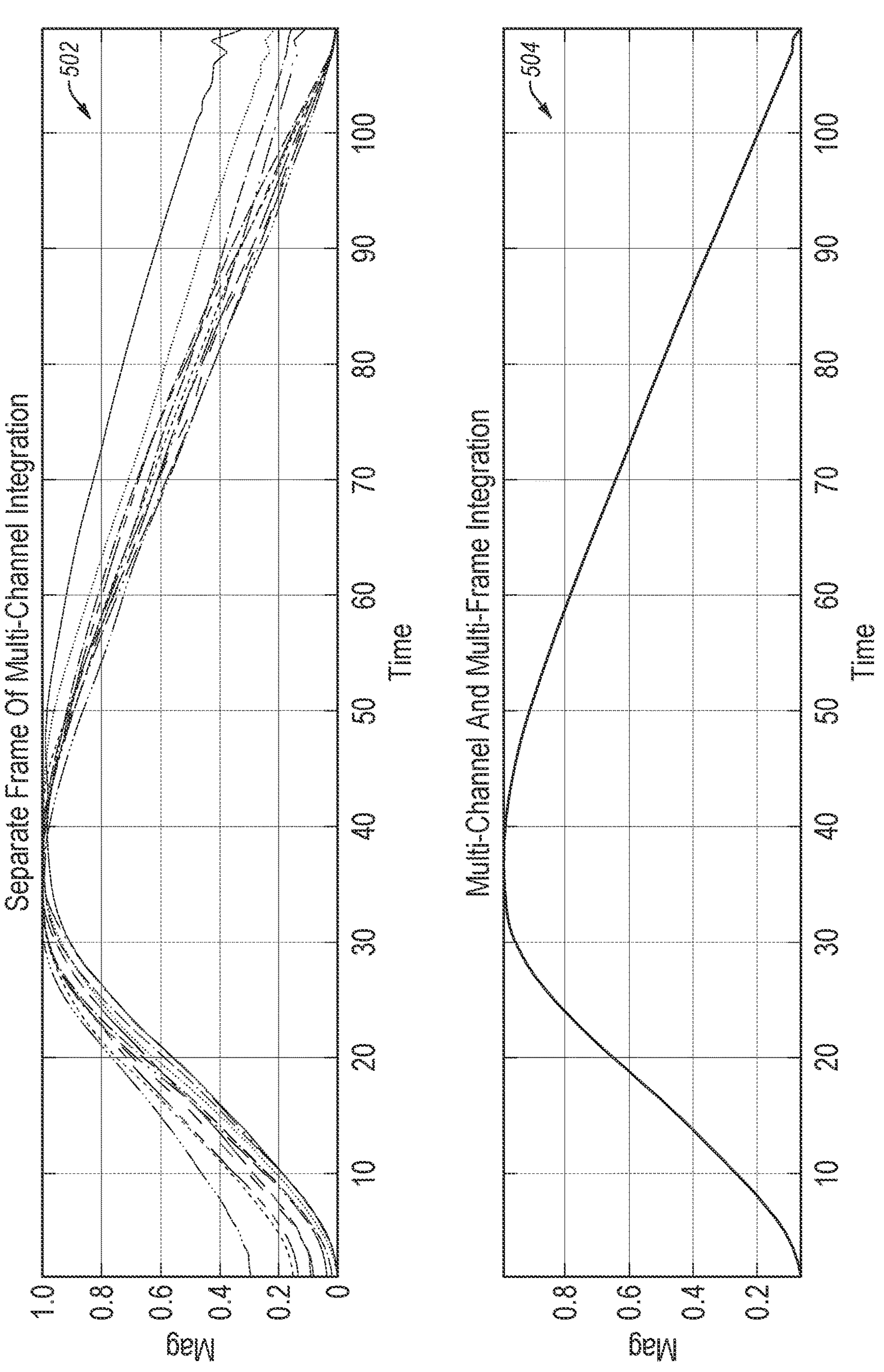
FIG. 5 illustrates multiple example optical signal pulse waves from an optical signal and an integrated optical signal pulse wave.

FIG. 5 illustrates multiple example optical signal pulse waves 502 from an optical signal and an integrated optical signal pulse wave 504, arranged in accordance with at least one embodiment herein. The optical signal that includes the optical signal pulse waves 502 may be generated by a multi-channel optical sensor. The integrated optical signal pulse wave 504 may be generated by integrating the optical signal pulse waves 502 over a time period, e.g., a time period when the subject is stationary or the optical signal is clean or likely to be clean. Features extracted from the integrated optical signal wave 504 may be more robust than features extracted from individual ones of the optical signal pulse waves 502.

Figure 6:
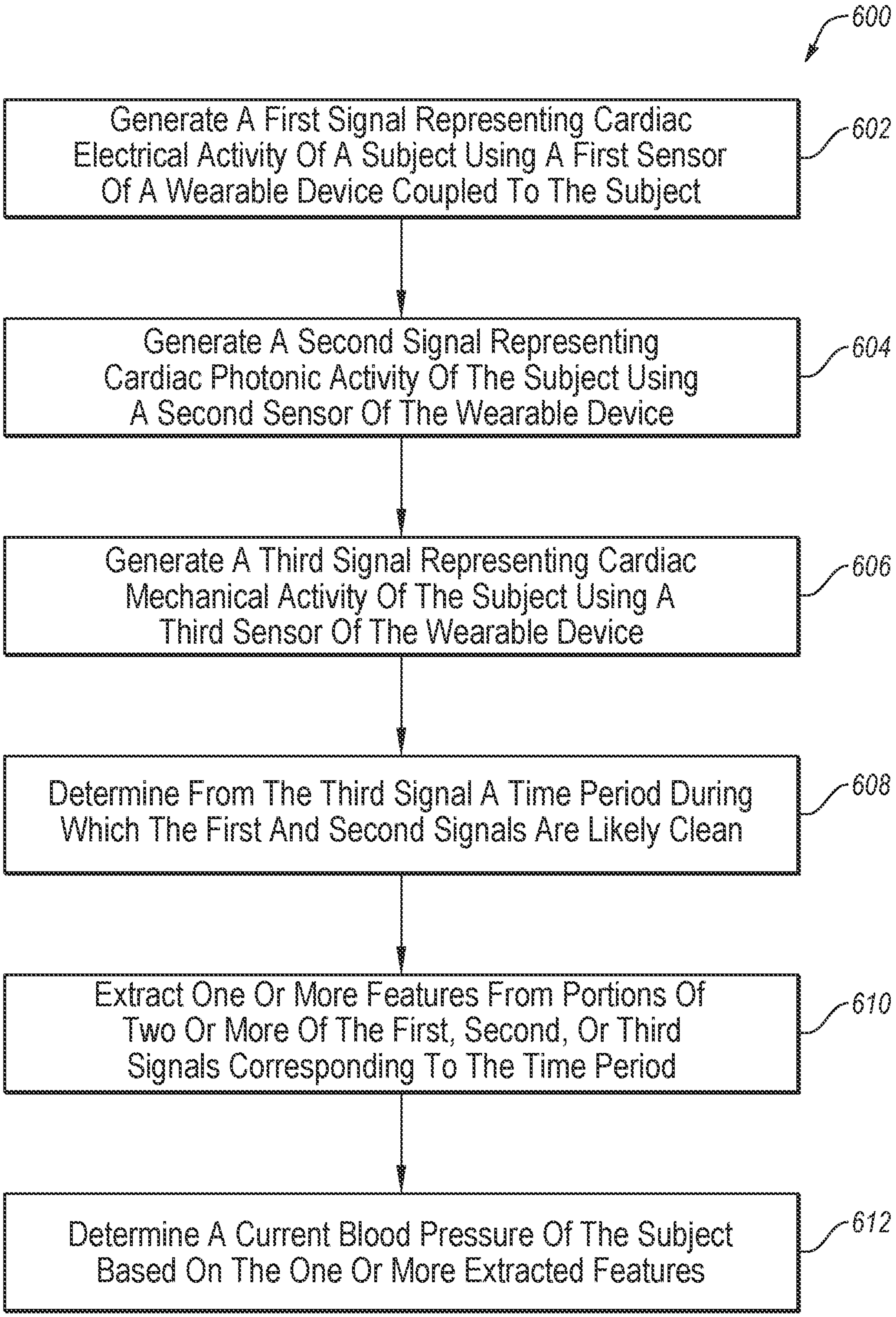
FIG. 6 is a flowchart of a method to monitor blood pressure of a subject.

FIG. 6 is a flowchart of a method 600 to monitor blood pressure of a subject, arranged in accordance with at least one embodiment described herein. The method 600 may be programmably performed or controlled by one or more processor devices in, e.g., one or more computing devices. In an example implementation, the method 600 may be performed and/or controlled in whole or in part by a wearable system such as the system 202, or a computing device such as the server 208 and/or a computing device 700 depicted in FIG. 7. The method 600 may include one or more of blocks 602, 604, 606, 608, 610, and/or 612.

At block 602, the method 600 may include generating a first signal representing cardiac electrical activity of the subject using a first sensor of a wearable system. The wearable system may include a wearable system such as the system 202. Generating the first signal at block 602 may include generating an ECG signal over multiple cardiac cycles of the subject using an ECG sensor, such as the ECG sensor 302. Block 602 may be followed by block 604.

At block 604, the method 600 may include generating a second signal representing cardiac photonic activity of the subject using a second sensor of the wearable system. Generating the second signal at block 604 may include generating an optical signal over the cardiac cycles of the subject using a pulse oximeter or other optical sensor, such as the optical sensor 304. Block 604 may be followed by block 606.

At block 606, the method 600 may include generating a third signal representing cardiac mechanical activity of the subject using a third sensor of the wearable system. Each of the first, second, and third sensors may be coupled to the subject at the same location (e.g., the subject's torso) or different locations (e.g., the first sensor and the third sensor may be coupled to the subject's chest and the second sensor may be coupled to the subject's arm) on skin of the subject using one or more adhesives, one or more adhesive patches, one or more straps, or other means. Generating the third signal at block 606 may include generating an accelerometer signal or an audio signal over the cardiac cycles of the subject using an accelerometer or acoustic sensor, such as the accelerometer 306 or microphone 308. Block 606 may be followed by block 608.

At block 608, the method 600 may include determining from the third signal a time period during which the first and second signals are likely clean. Determining from the third signal the time period during which the first and second signals are likely clean may include determining from the accelerometer signal or the audio signal a time period during which the subject is stationary. The time period may encompass two or more of the cardiac cycles of the subject. Block 608 may be followed by block 610.

At block 610, the method 600 may include extracting one or more features from portions of two or more of the first, second, or third signals corresponding to the time period during which the first and second signals are likely clean and/or during which the subject is stationary. The one or more extracted features may include at least one of a pulse transit time (PTT), a pulse arrival time (PAT), or one or more blood vessel elastics (BVE) features. Block 610 may be followed by block 612.

At block 612, the method 600 may include determining a current blood pressure of the subject based on the one or more extracted features. Determining the current blood pressure may include determining a current MAP, a current SBP, and/or a current DBP. In some embodiments, determining the current blood pressure based on the one or more extracted features, and potentially one or more additional extracted features, may be implemented as described in one or more of the references incorporated hereinabove by reference. Alternatively or additionally, block 612 may include determining, for each cardiac cycle of the subset encompassed by the time period, instantaneous blood pressure of the subject based on the corresponding PTT, PAT, or BVE feature(s) (and/or other features) extracted for the corresponding cardiac cycle; or determining average blood pressure of the subject based on an average of the PTTs, PATs, or BVE features (and/or other features) across the subset of two or more of the cardiac cycles.

In some embodiments, the method 600 may further include calibrating the wearable system with a prior blood pressure measurement generated by a blood pressure monitor at a prior time. For example, the system 202 may be calibrated with a prior blood pressure measurement generated by the blood pressure monitor 212. Calibrating the wearable system with the prior blood pressure measurement from the blood pressure monitor may include extracting a prior PTT, a prior PAT, or prior BVE features of the subject from portions of the first, second, and third signals corresponding to a prior time period that includes the prior time or that is within a threshold elapsed time (e.g., within 0.1, 0.5, 1, 2, seconds (or other threshold elapsed time)) of the prior time. Calibrating the wearable system may also include determining a relationship between the prior blood pressure measurement and the prior PTT, the prior PAT, or the prior BVE features. In this and other embodiments, determining the current blood pressure of the subject at block 612 may be further based on the determined relationship. In some embodiments, calibrating the wearable system may further include, prior to determining the prior PTT, the prior PAT, or the prior BVE features: generating the first, second, and third signals using the first, second, and third sensors of the wearable system during the prior time period; and determining from the third signal that the first and second signals are likely clean during the prior time period.

In some embodiments, the method 600 may further include extracting one or more additional features (e.g., in addition to the extracted PTT, PAT, and/or BVE features) from portions of two or more of the first, second, or third signals corresponding to the time period. In these and other embodiments, determining the current blood pressure of the subject at block 612 may be further based on the one or more additional extracted features. Extracting the one or more additional features may include extracting at least one of: a pressure constant k (PK) that is related to a total peripheral resistance (TPR) of a circulatory system of the subject; a photoplethysmography area (PA) that is associated with the TPR and changes in blood vessel tension of the subject; a rise time (RT) that is associated with contractile force and left ventricular function of the subject; a descent time (DT) that is associated with ventricular diastole of the subject; a pulsatile hetero height (PHH) that is associated with a magnitude of cardiac output of the subject; a pulse wave amplitude (peak); a systolic upstroke interval (Ts); or a diastolic interval (Td).

In some embodiments, the one or more extracted features extracted at block 610 include the PTT or the PAT and correspond to a cardiac cycle of the subject. The method 600 may further include determining one or more additional PTTs or one or more additional PATs corresponding to one or more additional cardiac cycles represented in portions of the first, second, and third signals corresponding to the time period when the first and second signals are likely clean. The method 600 may also include determining an average PTT from the PTT and the one or more additional PTTs or an average PAT from the PAT and the one or more additional PATs. In this and other embodiments, determining the current blood pressure at block 612 may be further based on the average PTT or the average PAT.

In some embodiments, the third signal includes an accelerometer signal and determining from the third signal the time period during which the first and second signals are likely clean includes determining from the third signal that the subject is stationary from a first time at or before a beginning of the time period to a second time at or after an end of the time period.

In some embodiments, the first and second sensors are respectively incorporated in first and second devices where the first device including the first sensor is configured to be coupled to a first location on the subject and the second device including the second sensor is configured to be coupled to a second location on the subject that is different than the first location. As an example, the first device may be configured to be coupled to a torso of the subject and the second device may be configured to be coupled to an appendage (e.g., finger, hand, arm, toe, foot, leg) of the subject. In these and other embodiments, the method 600 may further include wirelessly synchronizing the first and second devices to each other. The wireless synchronization may facilitate time alignment of measurement signals generated by each of the first and second sensors included in the first and second devices.

One skilled in the art will appreciate that, for this and other processes and methods disclosed herein, the functions performed in the processes and methods may be implemented in differing order. Further, the outlined steps and operations are only provided as examples, and some of the steps and operations may be optional, combined into fewer steps and operations, or expanded into additional steps and operations without detracting from the essence of the disclosed embodiments.

Accordingly, some embodiments described herein relate to methods of non-invasive continuous blood pressure monitoring that do not interfere with normal activities of a subject being monitored. Incorporation of an optical sensor and ECG sensor in the same wearable system allows determination and/or extraction of PTT, PAT, and/or other features from PPG and ECG signals for continuous blood pressure measurements without requiring the use of separate ECG and PPG devices (such as a corded fingertip PPG device) that can interfere with normal activities of the subject and require that the subject be stationary anytime measurements are being taken. Incorporation of an accelerometer and/or an acoustic sensor in the same wearable system as the optical sensor and ECG sensor may facilitate determining time periods when the subject is stationary or when signals generated by the optical sensor, ECG sensor, accelerometer, and/or acoustic sensor are otherwise clean or likely clean. Knowing when the subject is stationary and/or when measurement signals are clean or likely clean can be used to eliminate or reduce noise in the measurement signals and in corresponding blood pressure measurements determined thereby. For example, if a subject is sitting (e.g., watching TV, reading, or the like) or sleeping, there may be time periods of a few seconds, minutes, or hours when the subject is stationary (apart from movements of the subject's body arising from normal vital processes like respiration, cardiac activity, or the like) interrupted by occasional or infrequent movements (like coughing, adjusting sitting position, rolling over in bed) that may inject noise into the measurement signals. Accordingly, portions of the measurement signals with low or no noise or that are likely to have low or no noise may be identified and used in generating blood pressure measurements while portions that are noisy or likely to include noise may be discarded or otherwise eliminated from use in generating blood pressure measurements. The blood pressure measurements may be continuous for the time periods when the measurement signals have low or no noise or are likely to have low or no noise and may be interrupted, paused, or the like for the time periods when the measurement signals are noisy or are likely to include noise.

Figure 7:
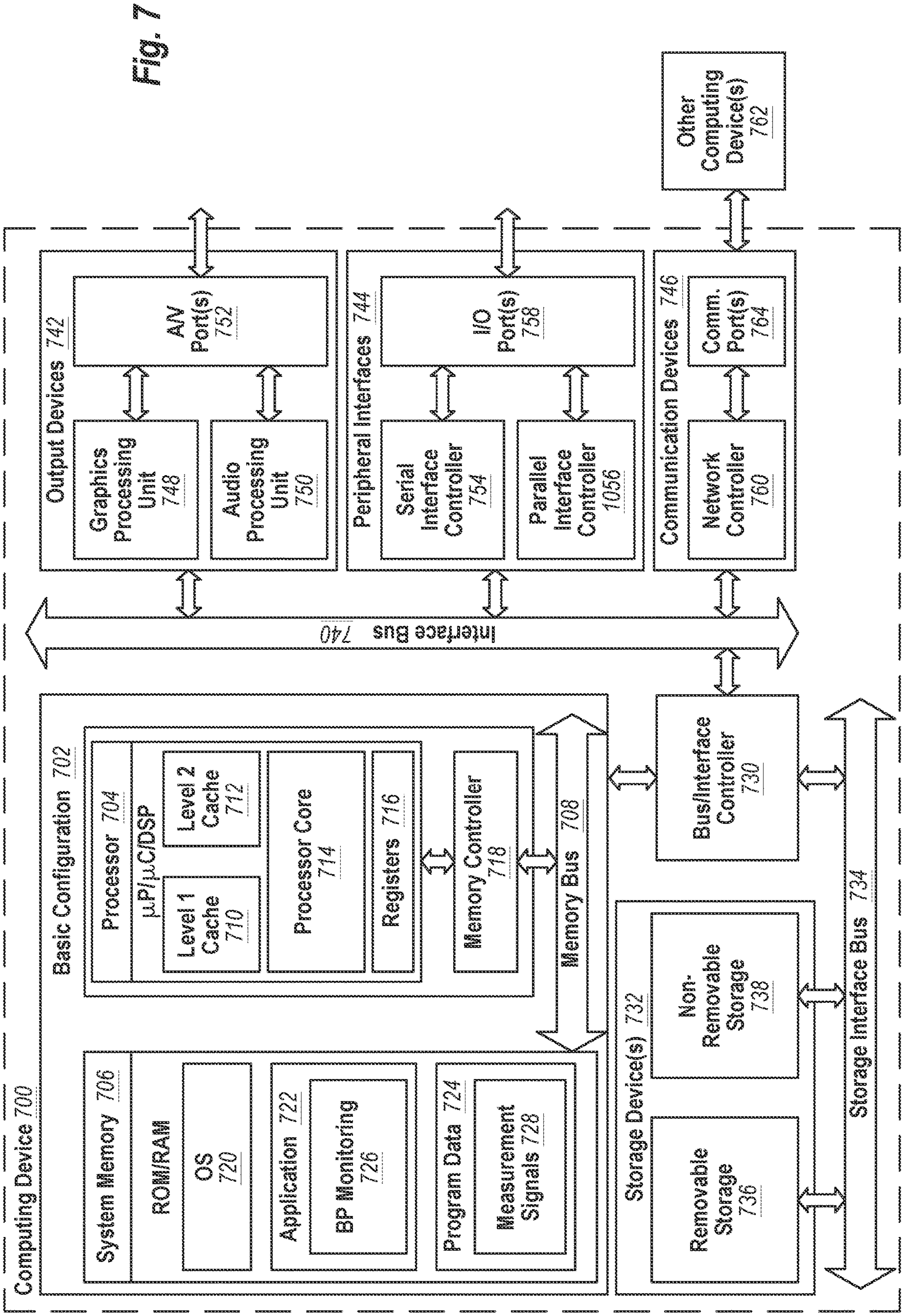
FIG. 7 is a block diagram illustrating an example computing device.

FIG. 7 is a block diagram illustrating an example computing device 700, arranged in accordance with at least one embodiment described herein. The computing device 700 may include, be included in, or otherwise correspond to, e.g., the system 202, the personal electronic devices 206, the server 208, and/or other devices described herein. In a basic configuration 702, the computing device 700 typically includes one or more processors 704 and a system memory 706. A memory bus 708 may be used to communicate between the processor 704 and the system memory 706.

Depending on the desired configuration, the processor 704 may be of any type including, but not limited to, a microprocessor (μP), a microcontroller (μC), a digital signal processor (DSP), or any combination thereof. The processor 704 may include one or more levels of caching, such as a level one cache 710 and a level two cache 712, a processor core 714, and registers 716. The processor core 714 may include an arithmetic logic unit (ALU), a floating point unit (FPU), a digital signal processing core (DSP Core), or any combination thereof. An example memory controller 718 may also be used with the processor 704, or in some implementations the memory controller 718 may include an internal part of the processor 704.

Depending on the desired configuration, the system memory 706 may be of any type including volatile memory (such as RAM), nonvolatile memory (such as ROM, flash memory, etc.), or any combination thereof. The system memory 706 may include an operating system 720, one or more applications 722, and program data 724. The application 722 may include a blood pressure (BP) monitoring application 726 that is arranged to perform or control performance of a method of monitoring blood pressure such as described herein. The program data 724 may include measurement signals 728 and/or sampled or digitized versions thereof for use in performance of the method of monitoring blood pressure. In some embodiments, the application 722 may be arranged to operate with the program data 724 on the operating system 720 such that one or more methods may be provided as described herein, including the method 600 of FIG. 6.

The computing device 700 may have additional features or functionality, and additional interfaces to facilitate communications between the basic configuration 702 and any involved devices and interfaces. For example, a bus/interface controller 730 may be used to facilitate communications between the basic configuration 702 and one or more data storage devices 732 via a storage interface bus 734. The data storage devices 732 may be removable storage devices

736, non-removable storage devices 738, or a combination thereof. Examples of removable storage and non-removable storage devices include magnetic disk devices such as flexible disk drives and hard-disk drives (HDDs), optical disk drives such as compact disk (CD) drives or digital versatile disk (DVD) drives, solid state drives (SSDs), and tape drives to name a few. Example computer storage media may include volatile and nonvolatile, removable and non-removable media implemented in any method or technology for storage of information, such as computer-readable instructions, data structures, program modules, or other data.

The system memory 706, the removable storage devices 736, and the non-removable storage devices 738 are examples of computer storage media or non-transitory computer-readable media. Computer storage media or non-transitory computer-readable media includes RAM, ROM, EEPROM, flash memory or other memory technology, CD-ROM, digital versatile disks (DVDs) or other optical storage, magnetic cassettes, magnetic tape, magnetic disk storage or other magnetic storage devices, or any other non-transitory medium which may be used to store the desired information and which may be accessed by the computing device 700. Any such computer storage media or non-transitory computer-readable media may be part of the computing device 700.

The computing device 700 may also include an interface bus 740 to facilitate communication from various interface devices (e.g., output devices 742, peripheral interfaces 744, and communication devices 746) to the basic configuration 702 via the bus/interface controller 730. The output devices 742 include a graphics processing unit 748 and an audio processing unit 750, which may be configured to communicate to various external devices such as a display or speakers via one or more A/V ports 752. The peripheral interfaces 744 include a serial interface controller 754 or a parallel interface controller 756, which may be configured to communicate with external devices such as input devices (e.g., keyboard, mouse, pen, voice input device, touch input device, etc.), sensors, or other peripheral devices (e.g., printer, scanner, etc.) via one or more I/O ports 758. The communication devices 746 include a network controller 760, which may be arranged to facilitate communications with one or more other computing devices 762 over a network communication link via one or more communication ports 764.

The network communication link may be one example of a communication media. Communication media may typically be embodied by computer-readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR), and other wireless media. The term "computer-readable media" as used herein may include both storage media and communication media.

The computing device 700 may be implemented as a portion of a small-form factor portable (or mobile) electronic device such as a smartphone, a personal data assistant (PDA) or an application-specific device. The computing device 700 may also be implemented as a personal computer including tablet computer, laptop computer, and/or non-laptop computer configurations, or a server computer including both rack-mounted server computer and blade server computer configurations. The computing device 700 may also be implemented as a wearable system, such as the wearable system 202 described herein.

Embodiments described herein may be implemented using computer-readable media for carrying or having computer-executable instructions or data structures stored thereon. Such computer-readable media may be any available media that may be accessed by a general-purpose or special-purpose computer. By way of example, such computer-readable media may include non-transitory computer-readable storage media including RAM, ROM, EEPROM, CD-ROM or other optical disk storage, magnetic disk storage or other magnetic storage devices, flash memory devices (e.g., solid state memory devices), or any other storage medium which may be used to carry or store desired program code in the form of computer-executable instructions or data structures and which may be accessed by a general-purpose or special-purpose computer. Combinations of the above may also be included within the scope of computer-readable media.

Computer-executable instructions may include, for example, instructions and data which cause a general-purpose computer, special-purpose computer, or special-purpose processing device (e.g., one or more processors) to perform a certain function or group of functions. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

Unless specific arrangements described herein are mutually exclusive with one another, the various implementations described herein can be combined to enhance system functionality or to produce complementary functions. Likewise, aspects of the implementations may be implemented in standalone arrangements. Thus, the above description has been given by way of example only and modification in detail may be made within the scope of the present invention.

With respect to the use of substantially any plural or singular terms herein, those having skill in the art can translate from the plural to the singular or from the singular to the plural as is appropriate to the context or application. The various singular/plural permutations may be expressly set forth herein for sake of clarity. A reference to an element in the singular is not intended to mean "one and only one" unless specifically stated, but rather "one or more." Moreover, nothing disclosed herein is intended to be dedicated to the public regardless of whether such disclosure is explicitly recited in the above description.

In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). Furthermore, in those instances where a convention analogous to "at least one of A, B, and C, etc." is used, in general, such a construction is intended in the sense one having skill in the art would understand the convention (e.g., "a system having at least one of A, B, and C" would include but not be limited to systems that include A alone, B alone, C alone, A and B together, A and C together, B and C together, or A, B, and C together, etc.).

Also, a phrase presenting two or more alternative terms, whether in the description, claims, or drawings, should be understood to include one of the terms, either of the terms, or both terms. For example, the phrase "A or B" will be understood to include the possibilities of "A" or "B" or "A and B."

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method to monitor blood pressure of a subject, the method comprising:

generating a first signal representing cardiac electrical activity of the subject using a first sensor of a wearable system;

generating a second signal representing cardiac photonic activity of the subject using a second sensor of the wearable system;

generating a third signal representing cardiac mechanical activity of the subject using a third sensor of the wearable system, the cardiac mechanical activity including closures of heart valves of the subject, wherein the first, second, and third sensors are coupled to a torso of the subject;

determining from the third signal a time period during which the subject is stationary;

extracting one or more features from portions of two or more of the first, second, or third signals corresponding to the time period during which the subject is stationary, the one or more extracted features comprising at least one of a pulse transit time (PTT), a pulse arrival time (PAT), or blood vessel elastics (BVE) features; and determining a current blood pressure of the subject based on the one or more extracted features.

2. The method of claim 1, further comprising calibrating the wearable system with a prior blood pressure measurement generated by a blood pressure monitor at a prior time.

3. The method of claim 2, wherein:

calibrating the wearable system with the prior blood pressure measurement from the blood pressure monitor comprises:

extracting a prior PTT, a prior PAT, or prior BVE features of the subject from portions of the first, second, and third signals corresponding to a prior time period that includes the prior time or that is within a threshold elapsed time of the prior time; and determining a relationship between the prior blood pressure measurement and the prior PTT, the prior PAT, or the prior BVE features; and determining the current blood pressure of the subject is further based on the determined relationship.

4. The method of claim 1, wherein determining the current blood pressure comprises determining at least one of a current mean arterial blood pressure (MAP), a current systolic blood pressure (SBP), or a current diastolic blood pressure (DBP).

5. The method of claim 1, further comprising extracting one or more additional features from portions of two or more of the first, second, or third signals corresponding to the time period during which the subject is stationary, wherein determining the current blood pressure of the subject is further based on the one or more additional extracted features.

6. The method of claim 5, wherein extracting the one or more additional features comprises extracting at least one of:

a pressure constant k (PK) that is related to a total peripheral resistance (TPR) of a circulatory system of the subject;

a photoplethysmography area (PA) that is associated with the TPR and changes in blood vessel tension of the subject;

a rise time (RT) that is associated with contractile force and left ventricular function of the subject;

a descent time (DT) that is associated with ventricular diastole of the subject;

a pulsatile hetero height (PHH) that is associated with a magnitude of cardiac output of the subject;

a pulse wave amplitude (peak);

a systolic upstroke interval (Ts); or a diastolic interval (Td).

7. The method of claim 1, wherein:

the one or more extracted features comprise the PTT or the PAT and correspond to a cardiac cycle of the subject;

the method further comprises:

determining one or more additional PTTs or one or more additional PATs corresponding to one or more additional cardiac cycles represented in portions of the first, second, and third signals corresponding to the time period during which the subject is stationary; and determining an average PTT from the PTT and the one or more additional PTTs or an average PAT from the PAT and the one or more additional PATs; and determining the current blood pressure is further based on the average PTT or the average PAT.

8. The method of claim 1, wherein at least one of: the first sensor comprises an electrocardiogram (ECG) sensor and generating the first signal comprises generating an ECG signal; the second sensor comprises a pulse oximeter and generating the second signal comprises generating a photoplethysmography (PPG) signal; or the third sensor comprises at least one of an accelerometer or an acoustic sensor and generating the third signal comprises generating at least one of an accelerometer signal or an audio signal.

9. The method of claim 1, wherein the third signal comprises an accelerometer signal and wherein determining from the third signal the time period during which the subject is stationary comprises determining from the third signal that the subject is stationary from a first time at or before a beginning of the time period during which the subject is stationary to a second time at or after an end of the time period during which the subject is stationary.

10. A non-transitory computer-readable storage medium having computer-executable instructions stored thereon that are executable by a processor device to perform or control performance of the method of claim 1.

11. A wearable system configured to be coupled to a subject, comprising:

a first sensor to detect cardiac electrical activity of a subject;

a second sensor to detect cardiac photonic activity of the subject;

a third sensor to detect cardiac mechanical activity of the subject;

a processor device communicatively coupled to each of the first sensor, the second sensor, and the third sensor; and a non-transitory computer-readable storage medium having computer-executable instructions stored thereon that are executable by the processor device to perform or control performance of operations to monitor blood pressure of a subject based on the cardiac electrical activity, cardiac photonic activity, and cardiac mechanical activity detected by the first, second, and third sensors;

wherein the operations comprise:

generating a first signal representing cardiac electrical activity of the subject using the first sensor;

generating a second signal representing cardiac photonic activity of the subject using the second sensor;

generating a third signal representing cardiac mechanical activity of the subject using the third sensor, the cardiac mechanical activity including closures of heart valves of the subject;

determining from the third signal a time period during which the subject is stationary;

extracting one or more features from portions of two or more of the first, second, or third signals corresponding to the time period during which the subject is stationary, the one or more extracted features comprising at least one of a pulse transit time (PTT), a pulse arrival time (PAT), or blood vessel elastics (BVE) features; and determining a current blood pressure of the subject based on the one or more extracted features.

12. The wearable system of claim 11, the operations further comprising calibrating the wearable system with a prior blood pressure measurement generated by a blood pressure monitor at a prior time.

13. The wearable system of claim 12, wherein calibrating the wearable system with the prior blood pressure measurement from the blood pressure monitor comprises:

extracting a prior PTT, a prior PAT, or prior BVE features of the subject from portions of the first, second, and third signals corresponding to a prior time period that includes the prior time or that is within a threshold elapsed time of the prior time; and determining a relationship between the prior blood pressure measurement and the prior PTT, the prior PAT, or the prior BVE features; and determining the current blood pressure of the subject is further based on the determined relationship.

14. The wearable system of claim 11, wherein determining the current blood pressure comprises determining at least one of a current mean arterial blood pressure (MAP), a current systolic blood pressure (SBP), or a current diastolic blood pressure (DBP).

15. The wearable system of claim 11, the operations further comprising extracting one or more additional features from portions of two or more of the first, second, or third signals corresponding to the time period during which the subject is stationary, wherein determining the current blood pressure of the subject is further based on the one or more additional extracted features.

16. The wearable system of claim 11, wherein extracting the one or more additional features comprises extracting at least one of:

a pressure constant k (PK) that is related to a total peripheral resistance (TPR) of a circulatory system of the subject;

a photoplethysmography area (PA) that is associated with the TPR and changes in blood vessel tension of the subject;

a rise time (RT) that is associated with contractile force and left ventricular function of the subject;

a descent time (DT) that is associated with ventricular diastole of the subject;

a pulsatile hetero height (PHH) that is associated with a magnitude of cardiac output of the subject; or a pulse wave amplitude (peak).

17. The wearable system of claim 11, wherein:

the one or more extracted features comprises the PTT or the PAT and correspond to a cardiac cycle of the subject;

the operations further comprise:

determining one or more additional PTTs or one or more additional PATs corresponding to one or more additional cardiac cycles represented in portions of the first, second, and third signals corresponding to the time period during which the subject is stationary; and determining an average PTT from the PTT and the one or more additional PTTs or an average PAT from the PAT and the one or more additional PATs; and determining the current blood pressure is further based on the average PTT or the average PAT.

18. The wearable system of claim 11, wherein at least one of:

the first sensor comprises an electrocardiogram (ECG) sensor and generating the first signal comprises generating an ECG signal;

the second sensor comprises a pulse oximeter and generating the second signal comprises generating a photoplethysmography (PPG) signal; or the third sensor comprises at least one of an accelerometer or an acoustic sensor and generating the third signal comprises generating at least one of an accelerometer signal or an audio signal.

19. The wearable system of claim 11, wherein:

the third signal comprises an accelerometer signal; and determining from the third signal the time period during which the subject is stationary comprises determining from the third signal that the subject is stationary from a first time at or before a beginning of the time period during which the subject is stationary to a second time at or after an end of the time period during which the subject is stationary.

20. The wearable system of claim 11, wherein:

the first sensor is incorporated in a first device of the wearable system that is configured to be coupled to a first location on the subject;

the second sensor is incorporated in a second device of the wearable system that is configured to be coupled to a second location on the subject that is different than the first location; and the first and second devices are configured to wirelessly synchronize to each other.

21. The wearable system of claim 20, wherein:

the first device is configured to be coupled to a torso of the subject; and the second device is configured to be coupled to an appendage of the subject.

22. A method to monitor blood pressure of a subject, comprising:

generating an electrocardiogram (ECG) signal over a plurality of cardiac cycles of the subject using an ECG sensor of a wearable device coupled to the subject;

generating an optical signal over the plurality of cardiac cycles using an optical sensor of the wearable system, wherein the ECG sensor and the optical sensor are integrated into the same wearable device;

generating an accelerometer signal or an audio signal over the plurality of cardiac cycles using an accelerometer or acoustic sensor of the wearable device, the accelerometer signal or audio signal capturing vibrations or sound energy from closures of heart valves of the subject;

determining from the accelerometer signal or the audio signal a time period during which the subject is stationary, the time period encompassing a subset of two or more of the plurality of cardiac cycles;

extracting, for each cardiac cycle of the subset, one or more features from portions of two or more of the ECG, optical, or accelerometer or audio signals corresponding to the time period during which the subject is stationary, the one or more extracted features for each cardiac cycle comprising at least one of a pulse transit time (PTT), a pulse arrival time (PAT), or blood vessel elastics (BVE) features; and one of:

determining, for each cardiac cycle of the subset, instantaneous blood pressure of the subject based on the corresponding PTT, PAT, or BVE features extracted for the corresponding cardiac cycle; or determining average blood pressure of the subject based on an average of the PTTs, PATs, or BVE features across the subset of two or more of the plurality of cardiac cycles.

23. The method of claim 1, wherein extracting one or more features from portions of two or more of the first, second, or third signals comprises extracting a PAT from portions of the second signal and the third signal.

24. The method of claim 1, further comprising extracting one or more additional features from portions of the third signal and one or both of the first and second signals, the portions corresponding to the time period during which the subject is stationary, wherein determining the current blood pressure of the subject is further based on the one or more additional extracted features.

25. The method of claim 1, further comprising detecting an S1 feature and an S2 feature in the third signal representing cardiac mechanical activity of the subject, the S1 feature detected as a vibration or sound energy produced when atrioventricular valves of the subject close at the beginning of systole and the S2 feature detected as a vibration or sound energy produced when semilunar valves of the subject close at the end of systole.

26. The method of claim 1, wherein the one or more extracted features comprises at least one of the PAT or the BVE features.

* * * * *